United States Patent
Conoir

(10) Patent No.: US 11,161,799 B2
(45) Date of Patent: Nov. 2, 2021

(54) METHOD FOR PURIFYING LIGHT ACRYLATES

(71) Applicant: Arkema France, Colombes (FR)

(72) Inventor: Pierre-Emmanuel Conoir, Saint Avold (FR)

(73) Assignee: Arkema France, Colombes (FR)

(*) Notice: Subject to any disclaimer, the term of this patent is extended or adjusted under 35 U.S.C. 154(b) by 0 days.

(21) Appl. No.: 17/254,876

(22) PCT Filed: Jun. 26, 2019

(86) PCT No.: PCT/FR2019/051569
§ 371 (c)(1),
(2) Date: Dec. 22, 2020

(87) PCT Pub. No.: WO2020/002830
PCT Pub. Date: Jan. 2, 2020

(65) Prior Publication Data
US 2021/0261491 A1    Aug. 26, 2021

(30) Foreign Application Priority Data

Jun. 27, 2018 (FR) ...................................... 18.55753

(51) Int. Cl.
| | | |
|---|---|---|
| *C07C 67/54* | (2006.01) | |
| *C07C 67/08* | (2006.01) | |
| *C07C 67/58* | (2006.01) | |
| *B01D 3/36* | (2006.01) | |
| *C07C 69/54* | (2006.01) | |

(52) U.S. Cl.
CPC .............. *C07C 67/54* (2013.01); *B01D 3/36* (2013.01); *C07C 67/08* (2013.01); *C07C 67/58* (2013.01); *C07C 69/54* (2013.01)

(58) Field of Classification Search
CPC ......... C07C 67/08; C07C 67/54; C07C 67/58; C07C 69/54; C07C 69/533; B01D 3/36
See application file for complete search history.

(56) References Cited

U.S. PATENT DOCUMENTS

| | | | |
|---|---|---|---|
| 5,866,713 A * | 2/1999 | Suzuki .................... | C07C 67/08 560/205 |
| 6,025,520 A | 2/2000 | Suzuki et al. | |
| 9,908,838 B2 * | 3/2018 | Tretjak .................... | C07C 45/52 |
| 2016/0272570 A1 * | 9/2016 | Tretjak .................... | C07C 67/58 |
| 2019/0127244 A1 * | 5/2019 | Zhou ........................ | B01D 3/36 |

FOREIGN PATENT DOCUMENTS

WO    WO2015/063388 A1    5/2015

OTHER PUBLICATIONS

Takashi Ohara et al, "Acrylic Acid and Derivatives", Ullmann's Encyclopedia of Industrial Chemistry Oct. 15, 2011 (Wiley-VCH,) pp. 8-9, Fig. 4.

* cited by examiner

*Primary Examiner* — Yate' K Cutliff
(74) *Attorney, Agent, or Firm* — Lynn B. Morreale

(57) ABSTRACT

The present invention relates to the production of light (meth)acrylic esters by direct esterification of acrylic acid by methanol or ethanol. The invention more particularly relates to a process for the recovery/purification of C1-C2 alkyl acrylate comprising the azeotropic distillation of the crude reaction mixture using a distillation column comprising a sidestream drawing off of a fraction rich in alkyl alkoxypropionate byproduct, the boiling point of which is close to that of acrylic acid, and therefore problematic in the purification process.

13 Claims, 2 Drawing Sheets

METHOD FOR PURIFYING LIGHT ACRYLATES

CROSS-REFERENCE TO RELATED APPLICATIONS

This application is a national stage application under 35 U.S.C. § 371 of PCT/FR2019/051569, filed Jun. 26, 2019, which claims benefit to application FR18.55753, filed Jun. 27, 2018.

TECHNICAL FIELD

The present invention relates to the production of light (meth)acrylic esters, such as methyl or ethyl (meth)acrylate, by direct esterification of (meth)acrylic acid by the corresponding light alcohol.

A subject matter of the invention is more particularly a process for the recovery/purification of $C_1$-$C_2$ alkyl acrylate comprising the azeotropic distillation of the crude reaction mixture using a distillation column comprising a sidestream drawing off of a fraction rich in alkyl alkoxypropionate byproduct, the boiling point of which is close to that of acrylic acid, and therefore problematic in the purification process.

PRIOR ART AND TECHNICAL PROBLEM

It is known to produce (meth)acrylic esters by carrying out an esterification reaction between an alcohol and a (meth)acrylic acid. This reaction is an equilibrated catalyzed reaction with generation of water. It is furthermore accompanied by side reactions which produce impurities.

It is necessary to remove the water produced in order to displace the equilibrium, to remove the impurities, as well as to recycle the unreacted reactants.

To this end, a set of distillations and/or of extractions, separations by settling, is generally carried out, which is both relatively complex to implement, in particular as a result of the presence of azeotropic mixtures, and costly in terms of energy.

The problems which arise during the manufacture of light (meth)acrylic esters, in particular $C_1$-$C_2$ alkyl acrylic esters, will now be set out, for convenience, on the basis of the example of methyl acrylate obtained by esterification of acrylic acid by methanol. However, the problems and the solution proposed by the invention can be applied to the use of ethanol in the esterification reaction.

By way of side reactions during the manufacture of methyl acrylate, unreacted acrylic acid can form oligomers, such as 3-acryloyloxypropionic acid (n=2) or 3-acryloyloxy-3-propoxypropionic acid (n=3), which are heavy byproducts with a higher boiling point than that of acrylic acid.

As other side reaction, a Michael addition can produce Michael adducts; in particular, a Michael addition between the methyl acrylate already formed and the methanol results in the formation of methyl methoxypropionate.

Methyl methoxypropionate (MMP) is a "heavy" byproduct because its boiling point (142° C., atmospheric P) is markedly greater than that of the methyl acrylate produced (80° C., atmospheric P), and it is formed in a significant amount in the process as the esterification reaction progresses, at the same time as the oligomers of acrylic acid.

Methyl methoxypropionate poses a problem because it exhibits a vapor pressure close to that of acrylic acid. Its boiling point is close to that of acrylic acid (144° C., atmospheric P), and it can form an azeotrope with water. It will be concentrated mainly in the recycling loop for the unreacted acrylic acid. It is then necessary to carry out a purging of this recycling loop, which can lead to a significant loss of acrylic acid. Furthermore, MMP is the lightest of the heavy byproducts compared to the acrylic acid oligomers; it can interfere in the final purification of the methyl acrylate and can detrimentally affect the quality of the finished product.

In order to limit the formation of methyl methoxypropionate, it has been proposed in the document U.S. Pat. No. 6,025,520 to carry out the esterification reaction under reduced pressure with an excess of acid. These conditions make it possible to improve the yield and the selectivity of the esterification reaction and to significantly reduce the formation of heavy byproducts generated by addition of methanol, such as methyl methoxypropionate, problematic for the line for purification of the desired ester.

The process described in the document WO 2015/063388 proposes to significantly reduce the formation of alkyl alkoxypropionate during the synthesis of methyl or ethyl (meth)acrylate in a conventional fixed bed reactor technology by carrying out the esterification reaction at atmospheric pressure, under conditions where the acid is in excess with respect to the alcohol and where the hourly space velocities are high.

However, there still exists a need to remove the methyl methoxypropionate formed during the synthesis of the methyl acrylate, which is detrimental to the material balance of the process (loss of starting materials during the purges) and to the purification line (complexity to achieve a high purity).

Surprisingly, the inventors have discovered that it is possible to remove the methyl methoxypropionate by sidestream drawoff during the azeotropic distillation of the reaction mixture carried out in a single distillation column provided with a sidestream drawoff.

Furthermore, the inventors have found that this sidestream drawoff also makes it possible to purge a part of the water generated by the esterification reaction, thus promoting the shift in equilibrium of the reaction to improve the yield of the reaction, and avoiding the formation of a water recirculation loop.

One of the objectives of the present invention is thus to provide a process for the recovery/purification of methyl acrylate, and more generally of methyl or ethyl acrylate, making possible efficient removal of methyl methoxypropionate, in a simplified configuration and with an improved material balance.

SUMMARY OF THE INVENTION

A subject matter of the present invention is a process for the recovery/purification of $C_1$-$C_2$ alkyl acrylate from a reaction mixture resulting from the esterification of acrylic acid with an alcohol chosen from methanol and ethanol, characterized in that it comprises the azeotropic distillation of said reaction mixture using a distillation column comprising a sidestream drawoff of a fraction rich in alkyl alkoxypropionate byproduct.

The term azeotropic distillation is understood to mean the separation of an azeotrope (or azeotropic mixture) consisting of a ternary alkyl acrylate/alcohol/water mixture.

According to one embodiment, the alcohol is methanol, the alkyl acrylate is methyl acrylate, and the alkyl alkoxypropionate is methyl methoxypropionate (MMP).

According to one embodiment, the alcohol is ethanol, the alkyl acrylate is ethyl acrylate, and the alkyl alkoxypropionate is ethyl ethoxypropionate (EEP).

According to one embodiment, the drawing off of the fraction rich in alkyl alkoxypropionate is carried out in the liquid phase.

According to one embodiment, the drawing off of the fraction rich in alkyl alkoxypropionate is carried out in the upper half of the azeotropic distillation column.

According to one embodiment, the azeotropic distillation is carried out under a slight vacuum under a pressure which can range from 200 to 600 mmHg.

According to one embodiment, the temperature at the bottom of the azeotropic distillation column is less than 110° C., preferably less than 100° C.

According to one embodiment, an internal reflux is provided in the azeotropic distillation column.

According to one embodiment, an external reflux is provided in the azeotropic distillation column using a stream comprising alkyl acrylate, preferably using a stream comprising a content by weight of alkyl acrylate of greater than 90%.

According to one embodiment, the fraction rich in alkyl alkoxypropionate contains alkyl alkoxypropionate at a content by weight which can range from approximately 20% to approximately 50%.

According to one embodiment, the fraction rich in alkyl alkoxypropionate contains water at a content by weight which can range from approximately 20% to approximately 60%.

According to one embodiment, the process is chosen from processes of continuous, semi-continuous or batch type.

According to one embodiment, the reaction mixture results from the esterification of acrylic acid with a stoichiometric excess of alcohol.

According to one embodiment, the reaction mixture results from the esterification of acrylic acid with an alcohol under conditions of stoichiometric excess of acid.

According to one embodiment, the process according to the invention comprises the following stages:
  a) the azeotropic distillation of the reaction mixture using a first distillation column making it possible to separate, at the top, an azeotropic mixture comprising the alkyl acrylate, the unreacted alcohol and water and, at the bottom, a fraction comprising the unreacted acrylic acid and heavy byproducts, a fraction rich in alkyl alkoxypropionate byproduct being removed by sidestream drawoff;
  b) the separation of the bottom stream from the first distillation column into a stream comprising essentially the unreacted acrylic acid, this stream being recycled to the esterification reactor, and a stream comprising essentially heavy byproducts, which is subjected to a thermal cracking releasing a stream of economically upgradable products, which stream can be recycled;
  c) the liquid/liquid extraction of the top stream from the first distillation column with an aqueous stream making it possible to separate an organic phase, comprising essentially the alkyl acrylate, and an aqueous phase, the aqueous phase being distilled in order to recover, on the one hand, a fraction rich in alcohol which can be recycled to the reactor and, on the other hand, a fraction rich in water which can be used as aqueous stream in the liquid/liquid extraction stage;
  d) the purification of said organic phase making it possible to recover the purified alkyl acrylate.

According to one embodiment, the purification d) is carried out by distillation, using a purification system comprising at least one distillation column, preferably two distillation columns in series.

According to one embodiment, the purification d) is carried out using a purification system comprising at least one partition column.

The present invention makes it possible to overcome the disadvantages of the state of the art related to the formation of alkyl alkoxypropionate byproduct in a process for the synthesis of methyl acrylate or ethyl acrylate by direct esterification of acrylic acid with the corresponding alcohol.

The invention makes it possible to efficiently remove the alkyl alkoxypropionate and to reduce the losses of economically upgradable products generated by the purges imposed by the accumulation of alkyl alkoxypropionate in the purification line.

The invention also makes it possible to minimize the accumulation of water which is harmful to the productivity and the energy consumption of the process.

This is accomplished by virtue of the use of a distillation column provided with a sidestream drawoff under conditions which make it possible to facilitate the separation of the alkyl alkoxypropionate, during the azeotropic distillation of the reaction mixture.

Thus, the invention provides a simplified process for the production of high purity methyl or ethyl acrylate, and optimizes the material balance of the process.

DETAILED ACCOUNT OF THE INVENTION

The invention is now described in greater detail and in a nonlimiting way in the description which follows, in comparison with a process of the prior art.

For simplicity, the description is based on the example of methyl acrylate obtained by esterification of acrylic acid by methanol. However, the solution proposed by the invention applies in the same way to the use of ethanol in the esterification reaction.

Figure 1:
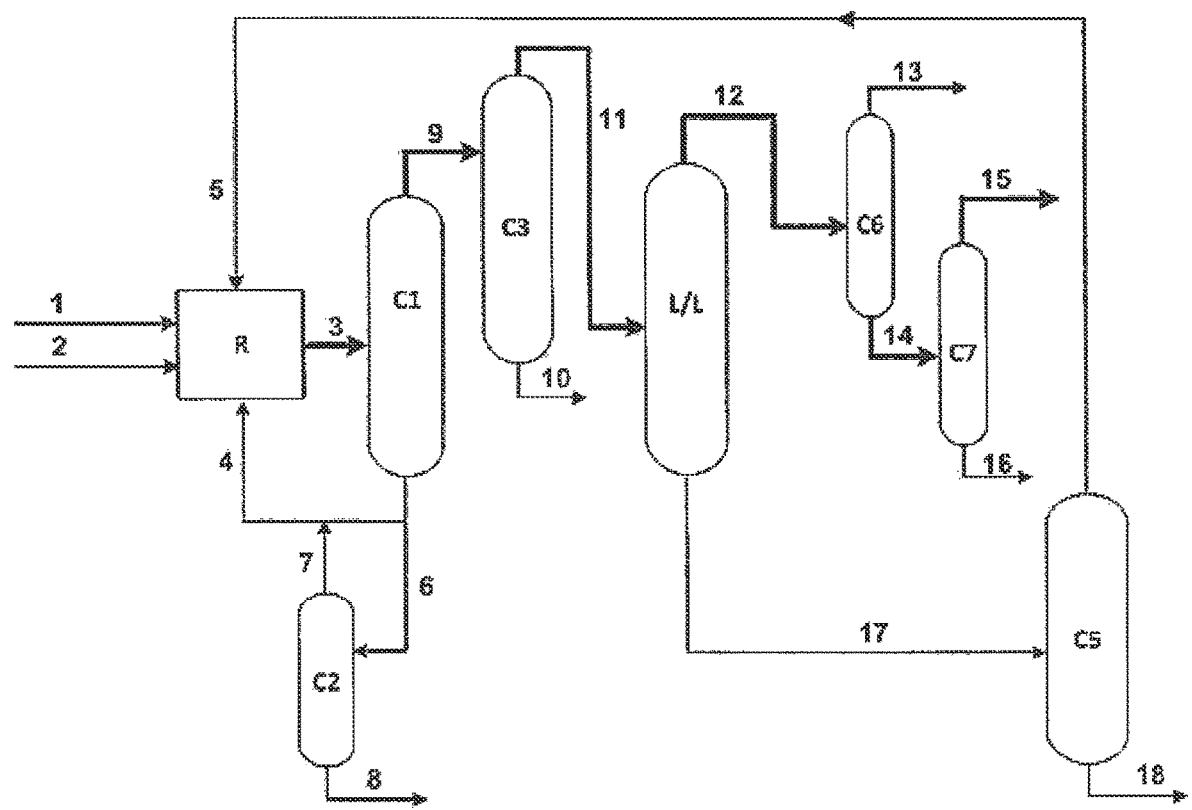
FIG. 1 diagrammatically represents a plant for the implementation of a process for the production of methyl acrylate according to the prior art.

A plant for the production of methyl acrylate of the prior art is represented in FIG. 1.

The reaction section comprises an esterification reactor R. The reactor R is fed by an acrylic acid feed pipe 1 and a methanol feed pipe 2. The reactor preferably contains a heterogeneous catalyst of acidic cation exchange resin type. In the case of homogeneous catalysis, the reactor is additionally fed by a catalyst feed pipe (not represented). The esterification reaction can be carried out in excess of methanol or in excess of acrylic acid.

At the outlet of the reactor R, the reaction mixture 3 is sent to an azeotropic distillation unit represented in FIG. 1 by two distillation columns in series C1 and C3, the first column C1 being connected to the second column C3 by the gas phase 9, and the second column C3 separating, at the bottom, a stream 10 of water consisting of a part of the water formed by the esterification reaction and of water injected in the form of steam into the column C3.

Alternatively, the azeotropic distillation unit comprises a single distillation column C1 operating under vacuum under the same conditions.

The distillation column C1 separates, at the bottom, a stream 6 comprising essentially unreacted acrylic acid, traces of light products (boiling point lower than that of acrylic acid), and heavy products having a higher boiling point than acrylic acid (oligomers of acrylic acid and Michael adducts).

The stream 6 is sent to a distillation column and/or a film evaporator C2 which separates a stream 7, comprising the residual acrylic acid and the lighter products, and a stream 8 consisting essentially of the heavy products. The stream 7 is advantageously recycled to the reactor R.

The stream 8 can be subjected to thermal cracking (not represented in FIG. 1) which makes it possible to recycle the noble products (starting compounds or finished product) potentially recoverable from the heavy products fraction. The thermal cracking is generally carried out at a temperature which can range, for example, from 120° C. to 220° C., optionally in the presence of an acid catalyst, such as sulfuric acid or a sulfonic acid.

The azeotropic distillation unit separates, at the top, a stream 11 consisting of an azeotropic mixture comprising the methyl acrylate formed, unreacted methanol and the water generated by the reaction, as well as light impurities and heavy impurities.

The methyl methoxypropionate MMP generated as byproduct during the esterification reaction exhibits the distinguishing feature of being found partly at the bottom of the azeotropic unit and partly in the mixture 11 extracted at the top of the azeotropic unit.

The complete removal of the MMP present in the stream 6 using the column and/or the film evaporator C2 is impossible owing to the fact that the vapor pressures with acrylic acid are very close. The MMP remains present partly in the stream 7 of acrylic acid which is recycled to the reactor and partly in the stream 8 which is subjected to thermal cracking, the effect of which on the dissociation of the MMP is generally limited.

The top stream 11 from the azeotropic distillation unit is sent to a liquid/liquid extraction section UL (settling tank or contactor) which generates, on the one hand, an aqueous phase 17 containing essentially methanol and, on the other hand, an organic phase 12.

The liquid/liquid extraction section generally consists of a liquid/liquid extraction column of packed column or stirred type, of a mixer-settling tank battery, of one or more settling tanks in series.

In the plant described in FIG. 1, the aqueous phase 17 is subjected to a distillation on a distillation column C5 in order to separate the methanol, which is recycled to the reactor (stream 5), it being possible for the aqueous stream 18 depleted in methanol to be recycled, for the liquid/liquid extraction phase.

The organic phase 12 can be subjected to one or more additional stages of distillation in series. For example, a topping column C6 extracts the residual light compounds 13 at the top and a tailing column C7 separates, at the bottom, a stream 16 comprising essentially the residual heavy compounds with methyl acrylate.

A stream 15 of purified methyl acrylate is extracted at the top of the final column of the purification line.

The MMP present in the stream 11 extracted at the top of the azeotropic unit is finally re-encountered mixed with methyl acrylate at the bottom of the tailing column C7 (stream 16).

In order to avoid losses of methyl acrylate, the stream 16 can be taken up by campaigns on the column and/or the film evaporator C2 in order to separate and recycle the methyl acrylate and to purge the MMP.

The process for the production of methyl acrylate according to the scheme represented in FIG. 1 is complicated to carry out and exhibits the disadvantage of accumulating methyl methoxypropionate at different points of the process. It is necessary to carry out purges at the end of the production campaign, causing losses of economically upgradable materials. This type of process generates significant losses of methyl acrylate if it operates continuously.

Figure 2:
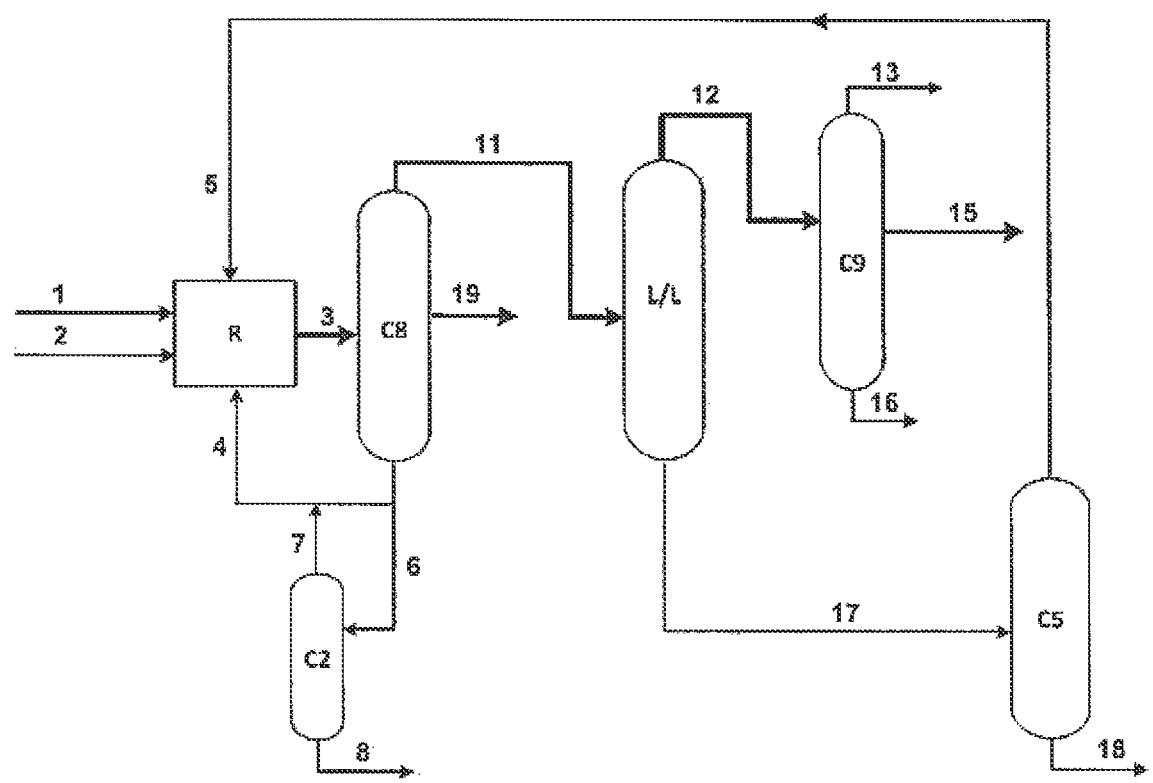
FIG. 2 diagrammatically represents a plant for producing methyl acrylate including the recovery/purification process according to the invention.

According to the invention, the azeotropic distillation unit consists of a single distillation column C8 provided with a sidestream drawoff to remove the MMP impurity, as shown in FIG. 2.

Use may be made, as distillation column C8, of a column comprising internal parts of the random or stacked packing type, of the dual flow plate, perforated plate having a weir or valve plate type.

The sidestream drawoff 19 is advantageously placed in the upper half of the distillation column.

The sidestream drawing off can be carried out in the liquid phase or in the gas phase; it is preferably carried out in the liquid phase in order to optimize the content of MMP extracted while limiting the drawing off of methyl acrylate.

The configuration of the distillation column C8 makes it possible to separate, at the top, a stream 11 consisting of an azeotropic mixture comprising the methyl acrylate formed, unreacted methanol and the water generated by the reaction, as well as light impurities and heavy impurities, at the bottom, a stream 6 comprising essentially unreacted acrylic acid, traces of light products, and heavy products, and a stream 19 drawn off as a sidestream.

The stream 19 comprises a large fraction of the MMP formed as a byproduct during the esterification. The stream 19 additionally comprises a part of the water generated by the esterification reaction. The sidestream drawoff thus makes it possible to purge a part of the water formed during the esterification. The sidestream drawoff prevents the accumulation of MMP, on the one hand, in the section for treatment of the stream 6 separated at the bottom of the azeotropic distillation column and, on the other hand, in the line for purification of the stream 11 comprising the methyl acrylate separated at the top of the azeotropic distillation column.

The stream 19 is a stream rich in MMP, that is to say that it contains approximately from 20% to 50% by weight of MMP, and can contain approximately from 20% to 60% by weight of water. The stream 19 can additionally contain methyl acrylate, methanol and acrylic acid in a low content.

The drawing off of the stream 19 optimizes the removal of the MMP while minimizing the removal of economically upgradable products within the process as a whole.

The stream 19 can advantageously be used as diluent for a stream of heavy products, or for conveying viscous streams, it being possible for these streams to be subjected to a thermal or catalytic cracking operation in order to recover the thus economically upgradable compounds.

Alternatively, the stream 19 can be subjected to a purification in order to recover the purified methyl methoxypropionate, on the one hand, and the economically upgradable compounds, such as methyl acrylate, methanol and acrylic acid, on the other hand.

The azeotropic distillation carried out using the distillation column C8 can be carried out under a pressure ranging from 200 to 600 mmHg, and at a temperature ranging from 50° C. to 110° C., preferably from 60° C. to 100° C.

Preferably, the temperature at the bottom of the column C8 is less than 110° C., in particular less than 100° C.

The distillation column can comprise a direct reflux or an external reflux (not represented in FIG. 2) provided by a stream comprising methyl acrylate, in particular by a part of the organic fraction 12 extracted at the top of the liquid/liquid extractor located downstream of the azeotropic distillation. Said stream is a stream concentrated in methyl acrylate, which can contain more than 90% by weight of methyl acrylate.

The treatment of the stream 6 can be carried out on a distillation column and/or a film evaporator C2 which separates a stream 7, comprising the residual acrylic acid and the lighter products, and a stream 8 consisting essentially of the heavy products, which is generally subjected to a thermal cracking.

According to the invention, the stream 7 of unreacted acrylic acid which is separated on the column and/or the film evaporator C2 contains only of the order of 10% by weight of MMP. The stream 7 is advantageously recycled to the reactor without risk of accumulation of MMP. In addition, the recycling of a small amount of MMP to the reaction contributes to limiting its formation in the reactor.

The stream 11 comprising the azeotropic mixture MA/methanol/water is sent to a liquid/liquid extraction section L/L (settling tank or contactor) which generates, on the one hand, an aqueous phase 17 containing essentially methanol and, on the other hand, an organic phase 12.

The liquid/liquid extraction section generally consists of a liquid/liquid extraction column of packed column or stirred type, of a mixer-settling tank battery, of one or more settling tanks in series.

The aqueous phase 17 can be subjected to a distillation on a distillation column C5 in order to recycle the methanol to the reactor (stream 5), it being possible for the aqueous stream 18 depleted in methanol to feed the extractor UL (not represented in FIG. 2).

The organic phase 12 is subjected to a purification line in order to recover the methyl acrylate with the purity necessary for its subsequent use. Generally, a purity of greater than 99.5%, indeed even of greater than 99.8%, is desired.

In order to do this, the organic phase 12 can be subjected to one or more additional stages of distillation in series, according to the methods known from the state of the art represented in FIG. 1. For example, a topping column C6 extracts the residual light compounds 13 at the top and a tailing column C7 separates, at the bottom, a stream 16 comprising essentially the residual heavy compounds with methyl acrylate.

According to one embodiment of the invention, the purification of the organic phase 12 is carried out using a purification system comprising at least one partition column. Represented in FIG. 2 is a single column C9 which separates, at the top, a stream 13 comprising the bulk of the light compounds and, at the bottom, a stream 16 comprising the bulk of the heavy compounds, and a stream 15 of purified methyl acrylate is drawn off as a sidestream.

An example of a purification system can comprise a partition column equipped with an internal partial partition creating separation zones in the column, and combined at the bottom with a single boiler and at the top with a single condenser, and a settling tank placed at the outlet of the top condenser. The partition column can comprise a common rectification section above the partition, a prefractionation section comprising the feeding of the column, a drawoff section separated from the prefractionation section by the partition comprising the drawing off of the purified ester, and a common reboiling section below the partition.

A mode of operation of such a purification system is in particular described in the document WO 2017/125657, which is incorporated by reference in the present invention.

According to the invention, the stream 16 comprising essentially the residual heavy compounds with methyl acrylate contains virtually no MMP. The stream 16 can be advantageously used for the preparation of the stabilizing solution injected at any point of the process in order to inhibit the polymerization reactions without risk of contamination by MMP; the stream 16 can be partly subjected by campaign to the treatment on the column and/or the film evaporator C2 in order to recover the methyl acrylate. The stream 16 can also be recycled partly on the column C8.

The methyl acrylate recovery/purification process according to the invention applies to a reaction mixture 3 resulting from the esterification of acrylic acid 1 with methanol 2 in the reactor R.

The esterification reaction can be carried out in excess of methanol; in this case, the acid/alcohol molar ratio is between 0.6 and 1; or in excess of acrylic acid; in this case, the acid/alcohol molar ratio is between 1.05 and 3; It being understood that the acid/alcohol molar ratio refers to the acid and alcohol contents of all of the streams feeding the esterification reactor (pure product streams and recycled streams).

The esterification reaction can be carried out under a pressure ranging from atmospheric pressure to a few bars, or under reduced pressure.

The esterification reaction is carried out in the presence of an acid catalyst, for example an acidic cation exchange resin in the case of heterogeneous catalysis; or, as catalyst in the case of homogeneous catalysis, use may be made, for example, of sulfuric acid or an organic sulfonic acid, such as methanesulfonic acid, para-toluenesulfonic acid, benzenesulfonic acid or dodecylsulfonic acid, or their mixtures. Preferably, the esterification reaction is carried out in heterogeneous catalysis, at atmospheric pressure.

The reaction is generally carried out in the presence of one or more polymerization inhibitors which are introduced into the reactor in a proportion of 500 to 5000 ppm, with respect to the crude reaction mixture. Mention may be made, as polymerization inhibitors which can be used, for example, of phenothiazine, hydroquinone, hydroquinone monomethyl ether, di(tert-butyl)-para-cresol (BHT), para-phenylenediamine, TEMPO (2,2,6,6-tetramethyl-1-piperdinyloxy), di(tert-butyl)catechol, or TEMPO derivatives, such as OH-TEMPO, alone or their mixtures in all proportions. A supplementary addition of polymerization inhibitor is generally carried out at the subsequent purification treatment.

The invention makes it possible to limit the losses of economically upgradable materials, such as acrylic acid, the alcohol or the alkyl acrylate, in a process for the production of light alkyl acrylate by direct esterification.

The following examples illustrate the present invention and do not have the aim of limiting the scope of the invention as defined by the appended claims.

EXPERIMENTAL PART

In the examples, the percentages are shown by weight, unless otherwise indicated, and the following abbreviations were used:
AA: acrylic acid
MA methyl acrylate
MMP: methyl methoxypropionate
MeOH: methanol Example 1 Purification of Methyl Acrylate by Simulation of a Process According to the Invention Simulations using a thermodynamic model were carried out for a reaction mixture obtained by reaction of acrylic acid with methanol in excess, on an acidic cationic resin.

The inlet flow rate of the reaction mixture in the purification line is adjusted in order to ensure a production of methyl acrylate MA of approximately 120 t/d. The flow rate of methyl methoxypropionate MMP to be purged is of the order of 80 kg/h, corresponding to the amount of MMP formed in the reaction at the rate of 120 t/d.

Two configurations were compared; they differ in the implementation of the azeotropic distillation:
- an azeotropic distillation in a single column under a slight vacuum (450 mmHg), the column comprising 16 theoretical stages and a sidestream drawoff located at stage 3 (according to the invention),
- an azeotropic distillation in the same distillation column under a slight vacuum, the column also comprising 16 theoretical stages but not comprising sidestream drawoff (reference).

In these 2 configurations, the azeotropic column top azeotropic mixture is subjected to the same liquid/liquid extraction treatment.

According to the simulations, a fraction of the MMP is purged via the bottom of the thermal cracker located at the bottom of the column C2, and a fraction of the MMP is purged at the bottom of the column C5 for distillation of the aqueous phase generated by the l/l extraction.

The distribution of the different MMP purge flow rates, expressed in kg/h, in the two configurations is compared in table 1 below.

TABLE 1

|  | Reference | Invention |
| --- | --- | --- |
| MMP purged at the bottom of the cracker | 14.7 | 14.6 |
| MMP purged at the bottom of column C5 | 13.9 | 2.9 |
| MMP purged in the stream 16 at the bottom of the MA purification column | 53.6 | 0 |
| MMP purged by sidestream drawoff | 0 | 66.9 |
| Total: | 82.2 | 84.4 |

The reference process creates a large MMP loop downstream of the azeotropic separation column, hence a higher proportion of MMP in the water purged at the bottom of the column C5.

The flow rate and the composition of the main MMP purge point in each of the two processes, respectively the stream 16 at the bottom of the column C7 in the reference process and the sidestream drawoff from the column C8 in the process according to the invention, are shown in table 2.

TABLE 2

|  | Reference | Invention |
| --- | --- | --- |
| Overall flow rate, kg/h | 250 | 200 |
| MMP, % | 21.4 | 33.4 |
| MA, % | 77.2 | 7.9 |
| AA, % | 0.2 | 3.2 |
| MeOH, % | 0 | 15.2 |
| Water, % | 0 | 39.1 |

In the reference process, the simulation indicates significant losses of MA which is 77% concentrated in the bottom of the tailing column C7. On the contrary, the sidestream drawoff installed on the azeotropic distillation column contains 33% MMP, 39% water and limited concentrations of economically upgradable products.

The sidestream drawoff of a fraction rich in MMP makes it possible to reduce the loss of MA by more than 80% with respect to a reference process, which represents a reduction in the consumption of the starting materials of the order of 20 kg of acrylic acid and 4 kg of methanol per tonne of MA produced, i.e. an economic gain of the order of E14 per tonne of methyl acrylate produced, without requiring costly modification to the plant.

Example 2 Purification by Means of a Pilot Plant Implementing the Process According to the Invention The pilot plant used employs a distillation column filled with structured packing elements equivalent to 25 theoretical stages.

It is fed in the lower part with 10 kg/h of synthetic reaction mixture (AA, MA, methanol, water, MMP) at approximately 50° C. The reflux is provided by a variable external flow rate of pure MA and the sidestream drawoff is carried out in the upper part. Stabilizers are injected at the top with the reflux and into the condenser (4-OH-TEMPO), as well as into the feed (PTZ).

The pressure at the column top is set at 450 mmHg.

The main action parameters are the amount of energy contributed to the reboiler of the column and the reflux flow rate of pure MA. They are modified with the aim of maximizing the concentration of MMP in the sidestream drawoff while limiting the concentration of AA at the column top.

The analysis of the compositions of the streams analyzed (feed, column top, sidestream drawoff and column bottom) shows that:
- virtually all of the AA present in the feed passes into the column bottom and the column top contains between 100 and 1000 ppm of AA;
- the MMP is a little lighter and up to 20% of the MMP present in the feed passes into the top and into the sidestream drawoff, depending on the operating conditions of the column;
- the column bottom stream contains from 10% to 20% water;
- the column bottom contains very little MA (500 to 2000 ppm) and methanol (2000 to 6000 ppm). These two entities very predominantly pass into the top and into the sidestream drawoff.

The results thus obtained have been combined in table 3. These results show that the sidestream drawoff is enriched in MMP and poor in economically upgradable compounds (MA, methanol, AA). Moreover, they validate the results of example 1, which are obtained by simulation.

TABLE 3

|  | Feed | Reflux | Top | Bottom | Sidestream drawoff |
| --- | --- | --- | --- | --- | --- |
| Flow rate (kg/h) | 10.0 | 5.7 | 10.7 | 5.0 | 0.03 |
| Methanol | 12.2% |  | 11.5% | 0.5% | 9.8% |
| MA | 32.5% | 100% | 83.0% | 0.2% | 8.6% |
| MMP | 8.5% |  | 0.7% | 14.3% | 38.2% |

TABLE 3-continued

|  | Feed | Reflux | Top | Bottom | Sidestream drawoff |
|---|---|---|---|---|---|
| AA | 33.3% |  | 0.1% | 67.8% | 0.1% |
| $H_2O$ | 13.4% |  | 4.7% | 17.2% | 43.3% |

The invention claimed is:

1. A process for the recovery/purification of $C_1$-$C_2$ alkyl acrylate from a reaction mixture resulting from the esterification of acrylic acid with an alcohol chosen from methanol and ethanol, said process comprising the step of azeotropically distilling said reaction mixture using an azeotropic distillation column comprising a sidestream drawoff of a fraction rich in alkyl alkoxypropionate byproduct.

2. The process as claimed in claim 1, wherein the sidestream drawing off of the fraction rich in alkyl alkoxypropionate is carried out in liquid phase.

3. The process as claimed in claim 1, wherein the drawing off of the fraction rich in alkyl alkoxypropionate is carried out in an upper half of the azeotropic distillation column.

4. The process as claimed in claim 1, wherein the azeotropic distillation is carried out under vacuum pressure ranging from 200 to 600 mmHg.

5. The process as claimed in claim 1, wherein a temperature at a bottom of the azeotropic distillation column is less than 110° C.

6. The process as claimed in claim 1, wherein an external reflux is provided in the azeotropic distillation column using a stream comprising alkyl acrylate.

7. The process as claimed in claim 1, wherein a fraction rich in alkyl alkoxypropionate contains alkyl alkoxypropionate at a content by weight ranging from 20% to 50%.

8. The process as claimed in claim 1, wherein a fraction rich in alkyl alkoxypropionate contains water at a content by weight ranging from 20% to 60%.

9. The process as claimed in claim 1, which is selected from the group consisting of continuous, semi-continuous and batch type processes.

10. The process as claimed in claim 1, comprising:
a) azeotropically distilling the reaction mixture using a first distillation column having a top and bottom to separate, at the top, an azeotropic mixture comprising alkyl acrylate, unreacted alcohol and water and, at the bottom, a fraction comprising unreacted acrylic acid and heavy byproducts, a fraction rich in alkyl alkoxypropionate byproduct being removed by sidestream drawoff;
b) separating a bottom stream from the first distillation column into a stream comprising unreacted acrylic acid which is recycled to an esterification reactor, and a stream comprising heavy byproducts, which is subjected to a thermal cracking releasing a stream of economically upgradable products which are recycled;
c) liquid/liquid extraction of a top stream from the first distillation column with an aqueous stream which is separated into an organic phase, comprising alkyl acrylate, and an aqueous phase, the aqueous phase being distilled in order to recover, on the one hand, a fraction rich in alcohol which is recycled to the reactor and, on the other hand, a fraction rich in water which is used as aqueous stream in the liquid/liquid extraction stage;
d) purifying said organic phase to recover the purified alkyl acrylate.

11. The process as claimed in claim 10, wherein purification step d) is carried out by distillation, using a purification system comprising at least one distillation column.

12. The process as claimed in claim 10, wherein purification step d) is carried out using a purification system comprising at least one partition column.

13. The process as claimed in claim 1, wherein the $C_1$-$C_2$ alkyl acrylate is methyl acrylate.

* * * * *